United States Patent [19]
Filmus et al.

[11] Patent Number: 5,171,850
[45] Date of Patent: Dec. 15, 1992

[54] INTESTINAL ONCOFETAL GENE

[75] Inventors: Jorge E. Filmus; Ronald N Buick, Toronto, Canada

[73] Assignee: The Ontario Cancer Institute, Toronto, Canada

[21] Appl. No.: 239,084

[22] Filed: Aug. 31, 1988

[51] Int. Cl.[5] ................ C12N 15/12; C07H 21/02; C07H 21/04
[52] U.S. Cl. ................................ 536/27; 435/6; 935/9
[58] Field of Search ....................... 435/6; 536/27

[56] References Cited

PUBLICATIONS

Filmus et al. Molecular and Cellular Biology 8(10):4243–4249, 1988.
Chemical Abstracts, vol. 107, No. 1, 1987, Abstract No. 1754p, Julien et al. Mol. Brain Res. vol. 1(3):243–250, 1986.
Chemical Abstracts, vol. 111, No. 3, 1989, Abstract No. 18541x, Filmus et al., Molecular and Cellular Biology, vol. 8, No. 10, pp. 4243–4249.
Quaroni and Isselbacher (1981) J. Natl. Cancer, Inst. 67:1353–1362.

Primary Examiner—Johnnie R. Brown
Assistant Examiner—Gary L. Kunz
Attorney, Agent, or Firm—Townsend and Townsend

[57] ABSTRACT

The preparation and use of polynucleotides and polypeptides corresponding to a novel gene expressed in fetal intestinal endoderm cells and the corresponding gene product, respectively, are disclosed. Expression of the gene, designated the intestinal oncofetal gene, is associated with neoplastic transformation in non-fetal intestinal cells other than adult crypt cells.

Clone OCI-5 was deposited at the American Type Culture Collection, 12301 Parklawn Drive, Rocksville, Maryland 20852, U.S.A., on Aug. 18, 1988, and granted accession No. 40481.

4 Claims, 4 Drawing Sheets a b c d e f    a b c d e f g 15 17 19 20 21  1 3 8 13 16 24    a b c d

```
5'      10                      30                      50                      70
GGTAGCGGCTCGTCTCTTGCTCTGCAAGGCTACTGCCAGACTTGCTGAGTCTCGGGACCGCTCCGGCTCTTA
        130                     150                     170                     190
GGGACCGTGCGCACCGCGTGCTTGCTGGTGGCGATGCTGCTCGGCTTGGGCTGCCTGGGACAGGCGCAGCCC
         GlyThrValArgThrAlaCysLeuLeuValAlaMetLeuLeuGlyLeuGlyCysLeuGlyGlnAlaGlnPro
        250                     270                     290                     310
AGACTGCAGCCCGGACTCAAATGGGTTCCAGAAACCCCTGTGCCAGGATCAGATTTGCAAGTATGTCTCCCC
ArgLeuGlnProGlyLeuLysTrpValProGluThrProValProGlySerAspLeuGlnValCysLeuPro
        370                     390                     410                     430
ACAGCGCGCCTGAACATGGAACAACTGCTCCAGTCTGCGAGTATGGAACTCAAGTTCTTAATTATTCAGAAT
ThrAlaArgLeuAsnMetGluGlnLeuLeuGlnSerAlaSerMetGluLeuLysPheLeuIleIleGlnAsn
        490                     510                     530                     550
AACTACACCAATGCCATGTTCAAGAATAACTACCCCAGCCTGACTCCACAAGCTTTTGAGTTTGTCGGTGAA
AsnTyrThrAsnAlaMetPheLysAsnAsnTyrProSerLeuThrProGlnAlaPheGluPheValGlyGlu
        610                     630                     650                     670
GATGATATGGTCAATGAATTGTTCGACAGCCTCTTTCCAGTGATCTATACCCAGATGATGAACCCAGGCCTC
AspAspMetValAsnGluLeuPheAspSerLeuPheProValIleTyrThrGlnMetMetAsnProGlyLeu
        730                     750                     770                     790
GACCTGAAAGTATTTGGCAGTTTCCCCAAGCTTATTATGACCCAGGTTTCCAAGTCACTGCAAGTTACTAGA
AspLeuLysValPheGlySerPheProLysLeuIleMetThrGlnValSerLysSerLeuGlnValThrArg
        850                     870                     890                     910
GACCACCTCAAGTTTAGTAAGGACTGTGGCCGTATGCTCACCCGAATGTGGTACTGCTCTTACTGCCAGGGA
AspHisLeuLysPheSerLysAspCysGlyArgMetLeuThrArgMetTrpTyrCysSerTyrCysGlnGly
        970                     990                    1010                    1030
GGCTGTATGGCAGGTGTGGTAGAGATCGACAAGTACTGGAGAGAATACATTCTGTCTCTTGAAGAGCTCGTG
GlyCysMetAlaGlyValValGluIleAspLysTyrTrpArgGluTyrIleLeuSerLeuGluGluLeuVal
       1090                    1110                    1130                    1150
TTTTCAACCATCCATGATTCCATCCAGTATGTGCAGAAGAACGGAGGCAAGCTGACCACCACTATTGGCAAG
PheSerThrIleHisAspSerIleGlnTyrValGlnLysAsnGlyGlyLysLeuThrThrThrIleGlyLys
       1210                    1230                    1250                    1270
GAAGATCTGTTTATTGACAAGAAGGTATTAAAAGTCGCCCGTGTCGAACATGAAGAAACCTTATCCAGCCGA
GluAspLeuPheIleAspLysLysValLeuLysValAlaArgValGluHisGluGluThrLeuSerSerArg
       1330                    1350                    1370                    1390
GCTTTGCCAGGCTACATCTGCAGCCATAGCCCCGTGGCCGAAAACGACACCCTGTGCTGGAACGGACAAGAG
AlaLeuProGlyTyrIleCysSerHisSerProValAlaGluAsnAspThrLeuCysTrpAsnGlyGlnGlu
       1450                    1470                    1490                    1510
CAGTTTAACCTCCATGAGCTGAAAATGAAGGGCCCTGAGCCAGTGGTTAGCCAGATCATTGACAAACTGAAG
GlnPheAsnLeuHisGluLeuLysMetLysGlyProGluProValValSerGlnIleIleAspLysLeuLys
       1570                    1590                    1610                    1630
GTGGATAAAAGCCTGGATGAGGAAGGACTTGAGAGTGGAGACTGTGGTGATGATGAGGATGAGTGCATCGGG
ValAspLysSerLeuAspGluGluGlyLeuGluSerGlyAspCysGlyAspAspGluAspGluCysIleGly
       1690                    1710                    1730                    1750
GCAGAACTGGCATATGATCTGGATGTGGACGATGCTCCAGGGAACAAGCAACATGGAAATCAGAAGGACAAC
AlaGluLeuAlaTyrAspLeuAspValAspAspAlaProGlyAsnLysGlnHisGlyAsnGlnLysAspAsn
       1810                    1830                    1850                    1870
ATCCTCATCAGTGTGGCCATCTACGTGGCGTGCTTTTTTCCTGGTGCACTGACTTGCCATGCCCATGCCTG
IleLeuIleSerValAlaIleTyrValAlaCysPhePheSerTrpCysThrAspLeuProCysProCysLeu
       1930                    1950                    1970                    1990
TCCTTTTTCTTTTCTTTTTTTTTTTACCTTGTATGCCTCCTCTCACCGCCATTAAGTAGGAGACTAACCAC
       2050                    2070                    2090                    2110
TTTAGTGGTAGGATAGATTGTCTTTTTTGCAAAAAAAAAAAAAACAAAAAAAAATTCAAGTTGTGCCAAATTAT
       2170                    2190                    2210
TCTCTTTCTCTGCATGGATTTCTTTGACAAAAAAAATAAATAAACATTCAAATAAAAAAA
                                                                                3'
```

*FIG. 8A.*

```
                         90                          110
TTGCCACTCTCTCGTGCT CTCCTCGCTACCCCAAGAAGCAGGATGGCC
                                                 MetAla
            210                         230
CCGCCGCCTCCAGACGCCACCTGTCACCAGGTCCGTTCTTTCTTCCAG
ProProProProAspAlaThrCysHisGlnValArgSerPhePheGln
            330                         350
AAGGGCCCAACATGCTGCTCAAGAAAGATGGAAGAAAAATACCAACTA
LysGlyProThrCysCysSerArgLysMetGluGluLysTyrGlnLeu
            450                         470
GCTGCCGGTTTTCCAAGAGGCCTTTGAAATTGTTGTTCGCCATGCCAAG
AlaAlaValPheGlnGluAlaPheGluIleValValArgHisAlaLys
            570                         590
TTTTTCACAGATGTGTCTCTCTACATCTTGGGTTCTGATATCAATGTG
PhePheThrAspValSerLeuTyrIleLeuGlySerAspIleAsnVal
            690                         710
CCCGAGTCAGTATTAGACATCAACGAGTGCCTCCGAGGAGCAAGACGC
ProGluSerValLeuAspIleAsnGluCysLeuArgGlyAlaArgArg
            810                         830
ATCTTCCTTCAGGCCCTGAACCTCGGAATTGAAGTAATCAACACCACC
IlePheLeuGlnAlaLeuAsnLeuGlyIleGluValIleAsnThrThr
            930                         950
CTGATGATGGTCAAACCTTGTGGTGGTTATTGCAATGTGGTCATGCAA
LeuMetMetValLysProCysGlyGlyTyrCysAsnValValMetGln
            1050                        1070
AACGGCATGTACAGAATCTACGACATGGAGAATGTGCTGCTCGGACTC
AsnGlyMetTyrArgIleTyrAspMetGluAsnValLeuLeuGlyLeu
            1170                        1190
TTGTGCGCCCACTCCCAGCAACGCCAATATAGATCTGCTTATTATCCT
LeuCysAlaHisSerGlnGlnArgGlnTyrArgSerAlaTyrTyrPro
            1290                        1310
AGAAGGGAACTGATTCAGAAGTTGAAGTCTTTCATCAGCTTCTATAGT
ArgArgGluLeuIleGlnLysLeuLysSerPheIleSerPheTyrSer
            1410                        1430
CTTGTGGAGAGATACAGCCAGAAGGCGGCAAGGAATGGGATGAAGAAT
LeuValGluArgTyrSerGlnLysAlaAlaArgAsnGlyMetLysAsn
            1530                        1550
CACATTAACCAGCTCCTGAGAACCATGTCTGTGCCCAAGGGTAAAGTT
HisIleAsnGlnLeuLeuArgThrMetSerValProLysGlyLysVal
            1650                        1670
AGCTCTGGTGACGGCATGATGAAAGTGAAGAACCAACTGCGCTTCCTT
SerSerGlyAspGlyMetMetLysValLysAsnGlnLeuArgPheLeu
            1770                        1790
GAGATCACCACCTCTCACAGCGTGGGGAACATGCCATCCCCACTGAAA
GluIleThrThrSerHisSerValGlyAsnMetProSerProLeuLys
            1890                        1910
TGCTGCCCTGCAGCACCTTGTGGCCCTCCTACATAAAGGGAGCCACCT
CysCysProAlaAlaProCysGlyProProThr
            2010                        2030
GTGTTATGTTTTCGAAAAATCAAATGGTATCTTTATGAGGAAGGTAAAT
            2130                        2150
TTTCTTACATTTGACTGCTGGAACATGGTTGTCATGGTTTCCCTCTTT
```

INTESTINAL ONCOFETAL GENE

BACKGROUND OF THE INVENTION

1. Field of the Invention

The present invention relates generally to methods and compositions useful for distinguishing neoplastic cells from normal cells. More particularly, the invention relates to the identification and preparation of polynucleotides and polypeptides useful in identifying the expression of a novel intestinal oncofetal gene in neoplastic cells.

With the advent of new and effective methods for cancer therapy, it has become increasingly important to be able to provide early diagnosis and to monitor the status of the cancer during the course of treatment. Many treatments, in order to be effective, must be commenced early in the course of the disease, and it is critical to monitor the tumor load during treatment in order to adjust the treatment regimen accordingly.

One approach to the diagnosis and monitoring of cancer is based on detecting the expression or presence of tumor antigens in biological specimens, particularly serum and tissue samples. Such tumor antigens, often referred to as tumor markers, are substances, typically proteins, glycoproteins, polysaccharides, and the like, which are produced by the tumor cells characteristic thereof. Often, the tumor marker may be produced by normal cells as well as tumor cells, but in the tumor cell the production has somehow become atypical. For example, production of the tumor marker may be greatly increased in the cancer cells, may be shed into circulation by the tumor cells, or the like.

Although a number of tumor markers have been identified in the past, no single tumor antigen has thus far provided an entirely reliable basis for cancer diagnosis and monitoring. Therefore, it is desirable to identify additional tumor markers which can be used singly or in combination with other tumor markers in the diagnosis and detection of cancer.

2. Description of the Background Art

Intestinal cell line IEC-18 was described by Quaroni and Isselbacher (1981) J. Natl. Cancer Inst. 67:1353-1362. This cell line was used in the preparation of the cDNA clone utilized to identify the novel intestinal oncofetal gene of the present invention.

SUMMARY OF THE INVENTION

The present invention provides compositions and methods useful for identifying neoplastic cells in a biological sample based on detection in mature cells of the expression of a novel gene normally expressed in the fetal intestinal endoderm. The gene is referred to hereinafter as the intestinal oncofetal gene. The compositions include isolated polynucleotides corresponding to the intestinal oncofetal gene and fragments thereof, labelled polynucleotides capable of hybridizing to the gene and acting as nucleic acid probes, polypeptides corresponding to the entire gene product or fragments thereof, and antibodies capable of specific binding to the gene product. The methods are based both on direct determination of gene expression, e.g., through detection of mRNA in the biological sample, and detection of the gene product in a biological sample, e.g., using immunological techniques specific for the gene product.

BRIEF DESCRIPTION OF THE DRAWINGS

FIG. 5 is a Northern blot analysis of clone OCI-5 in oncogene-transformed IEC-18 cells.

FIG. 8 is the complete nucleotide sequence and putative amino acid sequence of the novel intestinal oncofetal gene of the present invention.

DESCRIPTION OF THE SPECIFIC EMBODIMENTS

Figures 1, 3:
FIG. 1 is a Northern blot analysis of the expression of OCI-5 which is a cDNA clone of the novel intestinal oncofetal gene of the present invention.
FIG. 3 is a Northern blot analysis of the expression of the intestinal oncofetal gene in human cell lines. Lane f) represents cell line CaCo-2, a human colorectal cell line.

The compositions and methods of the present invention are based on the discovery of a novel gene expressed in fetal intestinal endoderm cells but down-regulated in more mature intestinal cells. The product of the novel gene may be involved in the cytoskeletal development of the cell or in cell attachment. The gene is widely conserved among animal species, particularly including human, rat, and mouse. Importantly, the gene has been found to be expressed in at least some non-fetal neoplastic cells so that detection of gene expression is diagnostic of neoplasia. The novel gene will be referred to hereinafter as the "intestinal oncofetal gene."

The mRNA transcript intestinal oncofetal gene will generally have a length in the range from about 2000 to 3000 bases, depending on the species of origin, usually being in the range from about 2400 to 2800 bases. In rat, the length is about 2600 bases including a non-translated region of approximately 500 bases. A complete sequence of a cDNA clone of the intestinal oncofetal gene (designated OCI-5) prepared from a rat intestinal cell line, as described in detail in the Experimental section hereinafter, is set forth in FIG. 8.

The intestinal oncofetal gene of the present invention may be obtained from intestinal cells of at least most other mammalian species, particularly including human, mouse, and rat, using OCI-5 (or other suitable nucleic acid sequences prepared as described hereinbelow) as a probe for screening a genomic library by conventional techniques. Alternatively, cDNA libraries may be screened to obtain cDNA clones of the gene.

Polynucleotides of the present invention include both DNA and RNA sequences corresponding to at least a portion of the intestinal oncofetal gene, usually including a sequence of at least about 10 bases which correspond to the gene and frequently including up to the entire length of the gene. The polynucleotides may also include bases which do not correspond to the intestinal oncofetal gene, for example, including control regions or linkers when the polynucleotide is going to be used to produce recombinant gene product and other regions which facilitate the manipulation and/or expression of the polynucleotide. The polynucleotide may also include the structural region of other unrelated genes, particularly when it is desired to produce a. fused gene product.

Correspondence between the polynucleotide and the intestinal oncofetal gene generally means that the polynucleotide will have a high degree of sequence homology with the naturally-occurring gene, usually having at least about 50% homology, more usually having at least about 75% sequence homology, and preferably having at least about 90% sequence homology. It will be appreciated, however, that such a high degree of sequence homology will not always be necessary, such as when the polynucleotide is being used as a portion of a recombinant DNA construct to produce polypeptides corresponding the natural gene product. Because of the redundant nature of the genetic code, substantial nucleotide substitutions can be made without significantly changing the amino acid constitution of the polypeptide being produced. It is only essential that the nucleotide encode the desired polypeptide, i.e., one having an amino acid sequence corresponding to the product of the naturally-occurring gene, as discussed in more detail below. In many cases, it may even be preferable to provide substitutions, e.g., when the recombinant DNA construct is to be expressed in a prokaryotic system, it will frequently be desirable to utilize codons preferentially recognized by the expression host. Additionally, correspondence intends that the single-stranded polynucleotides will be capable of hybridizing with either DNA strand of the naturally-occurring gene or to the mRNA transcripts produced from the gene, under varying degrees of stringency. This is of particular concern when the polynucleotide is being used as a nucleic acid probe.

Specific polynucleotide compositions according to the present invention include labelled nucleic acid probes useful for screening biological samples for the presence of the gene or the gene transcripts (mRNA) produced by expression of the gene. Such polynucleotide probes will be DNA or RNA polynucleotides or oligonucleotides or their analogs, which have sufficient complementarity with the target gene or mRNA so that stable binding can occur between the probe and the target. Homoduplexing is preferred, i.e., a perfect base match, but such is often not necessary when using longer probes. The degree of homology required for detectable binding also varies with the stringency of the hybridization medium and/or wash medium, as described in more detail hereinafter.

The length of the polynucleotide probes will usually be at least 10 bases, more usually being at least about 15 bases, frequently being in the range from about 50 to 100 bases, and preferably being in the range from about 200 to 600 bases or more. Conveniently, polynucleotides corresponding to the entire length of the intestinal oncofetal gene or cDNA derived from the gene, with or without plasmid vector sequences, may be labelled by nick-translation in the presence of labelled nucleotides and utilized as a probe.

Suitable DNA probes may be cloned in bacterial host cells following insertion into appropriate replication vectors, such as pBr322 or M13, or vectors containing RNA polymerase specific promoters, such as the SP6 promoter, and purified from the host cell by cell lysis and DNA extraction. Further purification, if desired, may be achieved by digestion with selected restriction enzymes, and further separation by gel or column fractionation techniques.

Suitable polynucleotide probes may, also be synthesized, chemically or enzymatically, using commercially-available methods and equipment. For example, solid phase phosphoramidite methods may be advantageously used for producing smaller probes. See, Caruthers et al., Cold Spring Harbor Symp. Quant. Biol. 47:411–418, 1982, and Adams et al. J. Am. Chem. Soc. 105:661, 1983, both of which are incorporated herein by reference. DNA probes can also be synthesized, for example, by reverse transcription of mRNA or produced by nick-translation of cloned intestinal oncofetal gene.

Methods for labelling the nucleic acid probes of the present invention are well described in the patent and scientific literature. The precise type of label employed will depend on the intended detection method. A common method of detection is the use of autoradiography with $^3H$, $^{125}I$, $^{35}S$, $^{14}C$, or $^{32}P$ autoradiography with labelled probes, and the like. Other labels include fluorophores, chemiluminescent agents, enzymes, and enzyme substrates. Usually, such labels will be directly conjugated to the probes, but may also be indirectly bonded through a ligand-anti-ligand complex, such as antibodies reactive with a liquid conjugated with label, avidin-biotin, or the like.

The nucleic acid probes of the present invention are useful in various in situ hybridization protocols for detecting the presence of particular genes or mRNA gene transcripts in biological samples, typically tissue samples. Such in situ hybridization techniques are well described in the technical literature, see, e.g., Singer et al. (1986) Biotechniques 4:230-250; Haase et al. (1984) Methods in Virology VII, pp. 189-226; and "Nucleic Acid Hybridization: A Practical Approach," eds. Hames and Higgins, IRL Press (1985) Washington, D.C., all of which are incorporated herein by reference.

In situ hybridization techniques may be carried out under various conditions of stringency during either the hybridization or the wash step. The precise degree of stringency is typically controlled by the ionic strength, partially denaturing solvents, and temperature of the solution. The stringency of hybridization or washing is conveniently varied by changing the polarity of the reactant solution through manipulation of the concentration of a partially denaturing solvent, such as formamide, within the range of about 20% to 50% by weight. Stringency can also be conveniently varied by changing salt concentration, usually from about 0.5 mM to typically up to a maximum of about 0.5 M, usually in the range from about 10 mM to 150 mM. Stringency can also be varied by changing temperatures, which will normally be in the range from about 20° to 75° C., more usually being in the range from about 20° to 37° C. The polynucleotides of the present invention will preferably have a sufficient degree of homology with the target polynucleotide, i.e., the intestinal oncofetal gene DNA or mRNA transcripts, so that hybridization may be carried out under relatively stringent conditions, allowing for high specificity of the test.

Polypeptides according to the present invention will be either haptenic or antigenic, including at least 6 amino acids, usually including at least 9 amino acids, and more usually including 12 or more amino acids found contiguously within the natural intestinal oncofetal gene product. Polypeptides will generally correspond to at least one epitopic site which is characteristic of the gene product, and will frequently include the entire gene product. By characteristic it is meant that the epitopic site will allow immunologic detection of the natural gene product in a physiological sample with reasonable assurance. Usually, it will be desirable that the epitopic site be immunologically distinct from (i.e., not cross-reactive with antibodies which recognize) other proteins which might be expected to be found in physiological samples of interest. In some case, however, it may be desirable that the epitopic site be immunologically similar to epitopic sites characteristic of other proteins.

The polypeptides of the present invention may be natural, i.e., including the entire intestinal oncofetal gene product or fragments thereof isolated from a natural source, or may be synthetic. The natural polypeptides may be isolated from fetal intestinal cells or other cellular sources of OCI-5 gene product by conventional techniques, such as affinity chromatography. Conveniently, polyclonal or monoclonal antibodies obtained according to the present invention (as described in more detail hereinbelow) may be used to prepare a suitable affinity column by well-known techniques. Such techniques are taught, for example, in Hudson and Hay, *Practical Immunology*, Blackwell Scientific Publications, Oxford, United Kingdom, 1980, Chapter 8.

Synthetic polypeptides which are immunologically cross-reactive with natural intestinal oncofetal gene product may be produced by either of two general approaches. First, polypeptides having fewer than about 150 amino acids, more usually fewer than about 100 amino acids, and typically fewer than about 80 amino acids, may be synthesized by the well-known Merrifield solid-phase method where amino acids are sequentially added to a growing chain (Merrifield (1963) J. Am. Chem. Soc. 85:2149-2156). Commercial systems for the automated synthesis of such polypeptides are available.

The second and generally preferred method for synthesizing polypeptides according to the present invention involves the expression in cultured cells of recombinant DNA molecules encoding all or a desired portion of the intestinal oncofetal gene. The portion of the oncofetal gene may itself be natural or synthetic, with natural genes and cDNA being obtainable from fetal intestinal cells, adult intestinal crypt cells, or cell lines, such as IEC-18, CaCO-2, RFL-6, and F9 as described in the Experimental section hereinafter. Alternatively, polynucleotides may be synthesized by well-known techniques, as described hereinabove. Double-stranded fragments may then be obtained either by synthesizing the complementary strand and then annealing the strands together under appropriate conditions, or by adding the complementary strand using DNA polymerase with an appropriate primer sequence. The required nucleotide sequence for rat polypeptides may be obtained from FIG. 8 hereinafter, making substitutions as desired within the limits of the degenerate genetic code.

The natural or synthetic DNA fragments coding for the desired intestinal oncofetal gene product or fragment may be incorporated in a DNA construct capable of introduction to an expression in vitro cell culture. Usually, the DNA constructs will be suitable for replication in a unicellular host, such as yeast or bacteria. They may also be intended for introduction and integration within the genome of cultured mammalian or other eukaryotic cells, typically by cotransfection with a marker selectable in the cells, such as the DHFR gene. DNA constructs prepared for the introduction into bacteria or yeast will include a replication system recognized by the host, the DNA coding the desired polypeptide product, transcriptional and translational initiation and regulatory sequences joined to the 5'-end of the DNA fragment, and transcriptional and translational termination regulatory sequences joined to the 3'-end fragment. The transcriptional regulatory sequences will include a heterologous promoter which is recognized by the host. Conveniently, a variety of suitable expression vectors are described in the scientific and patent literature and additional such vectors are commercially available for a number of hosts.

To be useful in the detection methods of the present invention, the polypeptides are obtained in substantially pure form, that is, typically from about 50% W/W (weight/weight) or more purity, substantially free from interfering proteins and contaminants. Preferably, the intestinal oncofetal polypeptides are isolated or synthesized in a purity of at least about 80% W/W, and more preferably, in at least about 95% W/W purity. Using conventional protein purification techniques, homogeneous polypeptide compositions of at least about 99% W/W purity can be obtained. For example, polypeptides may be purified by use of the antibodies subscribed hereinafter using the immunoadsorbent affinity columns described hereinabove.

Once a sufficient quantity of either natural or synthetic intestinal oncofetal polypeptides have been obtained, polyclonal antibodies specific for the intestinal oncofetal gene product may be produced by in vitro or in vivo techniques. The in vitro techniques involve in vitro exposure of lymphocytes to the antigenic polypeptides, while in vivo techniques require the injection of polypeptides into a wide variety of vertebrates. Suitable vertebrates are non-human, including mice, rats, rabbits, sheep, goats, and the like. Polypeptides having more than about 30 amino acids, usually more than about 50 amino acids, may serve directly as the immunogen, while haptenic polypeptides smaller than about 10 kD, particularly less than 6 kD, will generally be joined to a larger molecule to elicit the desired immune response. The immunogens are then injected into the animal according to a predetermined schedule, and the animals are bled periodically with successive bleeds having improved titer and specificity. Injections may be made intramuscularly, subcutaneously, or the like, and an adjuvant, such as incomplete Freund's adjuvant, will usually be employed. The polypeptide corresponding to the entire gene product can also be used as the immunogen, although selection of antibodies specific for a particular determinant or epitope will be more difficult.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the spleen removed; and the spleen cells immortalized. The manner of immortalization is not critical. Presently, the most common technique is fusion with a myeloma cell fusion partner, as first described by Kohler and Milstein (1976) Eur. J. Immunol. 6:511-519. Other techniques for immortalization include EBV transformation, transformation with oncogenes, retroviruses, and the intenance of the cell line and production of monoclonal antibodies. For specific methodologies for producing monoclonal antibodies from polypeptides, see Goding, *Monoclonal Antibodies: Principles and Practice*, Academic Press, 2nd ed. (1986), the disclosure of which is incorporated herein by reference.

When employing fusion with a fusion partner, the manner of fusion is not critical and various techniques may be employed. Conveniently, the spleen cells and myeloma cells are combined in the presence of a non-ionic detergent, usually polyethylene glycol, and other additives, such as Dulbecco's Modified Eagle's Medium, for a few minutes. At the end of the fusion, the non-ionic detergent is rapidly removed by washing the cells. The fused cells are promptly dispensed in small culture wells (usually in a microtiter plate at relatively low density, ranging from about 1 to $5 \times 10^5$ cells/well), in a selective medium chosen to support growth of the hybrid cells while being lethal to the myeloma cells. Usually, the myeloma cell line has been mutated to be sensitive to a lethal agent, typically being HAT sensitive, and the medium includes a HAT concentration sufficient to inhibit the proliferation of the unfused myeloma cells.

After a sufficient time, usually from about 1 to 2 weeks, colonies of hybrids are observed in plates containing hyperpositive wells are identified. The plates and wells having only one colony per well are selected, and supernatants from these wells are tested for binding activity against the intestinal oncofetal gene product or a polypeptide corresponding thereto. Once positive hybridomas are identified, the cell line can be maintained as a viable culture and/or a quantity of the cells may be grown out, separated, and stored by lyophilization.

Depending on the desired use for the antibodies, further screening of the hybridomas may be desirable. For use in immunodiagnostic assays, antibodies having very high specificity and affinity for the antigenic site are desirable.

Once the desired hybridomas have been selected, monoclonal antibodies may be isolated from supernatants of the growing colonies. The yield of antibodies obtained, however, is usually low. The yield may be enhanced by various techniques, such as injection of the hybridoma cell line into the peritoneal cavity of a vertebrate host. Monoclonal antibodies may then be harvested from the ascites fluid or the blood. Proteinaceous and other contaminants will usually be removed from the monoclonal antibodies prior to use by conventional techniques, e.g., chromatography, gel filtration, precipitation, extraction, or the like.

The polypeptides and antibodies as just described may be used with or without modification for the detection of the intestinal oncofetal gene product. Frequently, the polypeptides and/or antibodies will be labelled by joining, either covalently or non-covalently, a substance which provides for a detectable signal. A wide variety of labels and conjugation techniques are known for polypeptides and antibodies and are reported extensively in both the scientific and patent literature. Some of the labels include radionuclides, enzymes, enzyme substrates, co-factors, inhibitors, fluorescers, chemiluminescers, magnetic particles, and the like. Patents teaching the use of such labels include U.S. Pat. Nos. 3,817,837; 3,850,752; 3,939,350; 3,996,345; 4,277,437; 4,275,149; and 4,366,241, the disclosures of which are incorporated herein by reference.

The compositions of the present invention, as just described, are useful for determining the expression of the intestinal oncofetal gene, or presence of the oncofetal gene product, in physiological samples, such as tissue, blood, plasma, serum, urine, sputum, saliva, semen, and the like. Nucleic acid probes will be particularly useful for detecting the presence of the intestinal oncofetal gene in such samples, more particularly for detecting expression of the gene in the sample. Gene expression in non-fetal samples (other than adult crypt cells where normal expression may be observed) is diagnostic of neoplasia. The polypeptides and antibodies will be particularly useful in performing immunologic techniques for detecting the intestinal oncofetal gene product directly in such samples. In particular, such immunologic techniques will be valuable for detecting the gene product in tissue samples, particularly primary and metastatic tumor tissue samples suspected of intestinal origins.

For hybridization with nucleic acid probes, the physiological sample will be prepared by, standard techniques (depending on the nature of the sample) and contacted with a hybridization solution, and the cells thereafter introduced into a wash solution having a predetermined concentrations of salts, buffers, and detergents. The time period for the wash may vary from 5 minutes to several hours or more. Typically it is the wash solution that most often determines the stringency and facilitates dissociation of mismatched duplexes. After washing the hybridization complexes at room temperature with dilute buffered sodium chloride solution, the complex may be assayed for the presence of duplexes (e.g., bound probes) in accordance with the nature of the label. Such detecting step typically will be completed in from about 1 to 24 hours, depending on the nature of the detection system.

Immunoassays and Western blot analyses will also find use in detecting the expression of the intestinal oncofetal gene product in patient samples, such as tissue, blood, and urine. Use of antibodies in protein binding assays is well established. Numerous competitive and non-competitive binding assays have been described in the scientific and patent literature, and a large number of such assays are commercially available. Immunohistochemical techniques will also find use for the detection of the gene product in tissue samples. Such techniques are also well described in the patent and scientific literature. A particularly useful technique is described in U.S. Pat. No. 4,684,609, the disclosure of which is incorporated herein be reference.

The following examples are offered by way of illustration, not by way of limitation.

EXPERIMENTAL

Cell Lines and Culture

The following cell lines were used in these experiments: IEC-18 (Quaroni and Isselbacher (*1981*) J. Natl. Cancer Inst. 67:1353–1362) and IEC-14 (Quaroni et al. (1979) J. Cell Biol. 80:248–265), derived from normal rat small intestine; NRK-52E, derived from normal rat kidney; F9, derived from rat teratocarcinoma (Strickland and Mahdavi (1978) Cell 15:393–403); Rat-II, derived from normal rat fibroblasts (Topp (1981) Virology 113:408–411); CaCo-2, HT-29, DLD-1, derived from human colon carcinomas; MDA-468, derived from human breast adenocarcinoma (Pathak et al. (1979) J. Natl. Cancer Inst. 62:263–271); SKMG-3, derived from human glioblastoma (Pfreundschuh et al. (1978) PNAS USA 5:5122–5126); HOC-8, derived from a human ovarian adenocarcinoma (Filmus et al. (1986) Can. Res. 6:5179–5182); and 427N, derived from normal human fibroblasts. NRK-52E, CaCo-2, HT-29 and DLD-1 were obtained from the American Type Culture Collection.

The induction of differentiation of F9 teratocarcinoma cells into visceral and parietal endoderm-like cells was performed as described (Hogan et al. (eds.) (1986) "Manipulating the Mouse Embryo" Cold Spring Harbor Laboratory, N.Y.) using retinoic acid alone or dibutyril cAMP/retinoic acid, respectively.

Preparation of the cDNA Library

A cDNA library was made from poly(A)+RNA obtained from IEC-18 cells using the lambda gt10 cloning system as previously described (Okayama and Berg (1982) Mol. Cell Biol. 2:161–169). 20,000 plaques were transferred onto duplicate nitrocellulose filters (1,000 plaques/filter). For preparation of enriched probes (Hedrick et al. (1984) Nature 308:149–153), 32P-labelled single stranded cDNA reverse transcribed from 3 ug of IEC-18 poly(A)+RNA was annealed for 40 hrs at 68° C. to 25 ug of NRK-52E poly(A)+RNA in a volume of 12 ul, containing 0.5 M sodium phosphate buffer pH 7.0, 1 mM EDTA, and 0.1% SDS in a sealed siliconized glass capillary. This mix was then diluted into 1 ml of 0.12 M sodium phosphate buffer containing 0.1% SES and passed over a column of 0.2 g hydroxyapatite to separate the single stranded cDNA from the double stranded. The eluate containing the single stranded cDNA was used to screen the 20,000 recombinant phages on nitrocellulose filters. Hybridization was carried out at 65° C. in 6X SSC, 1X Denhardts solution, and 200 μg/ml denatured salmon sperm DNA. A duplicate set of nitrocellulose filters was hybridized with a 32P-labelled single stranded cDNA prepared from NRK-52E mRNA using the same conditions as used for the IEC-18 subtracted probe.

Eighty percent of the IEC-18 cDNA hybridized with the NRK-52E mRNA. The remaining 20% of the cDNA was used to screen one set of the nitrocellulose filters blotted with the IEC-18 cDNA library. The other set of the filters were screened with single stranded cDNA prepared from NRK-52E mRNA. Plaques that were positive when probed with the IEC-18 subtracted cDNA and negative with NEK-52E cDNA were selected for a secondary screening. Five of these plaques showed similar results in the secondary screening and were selected for further studies.

RNA Isolation and Blotting

Total RNA was isolated from cultured cells by guanidine isothiocyanate solubilization and centrifugation over a CsCl cushion. Poly(A)+RNA was purified by passage over oligo(dT)-cellulose. The RNA was denatured with glyoxal and dimethyl sulfoxide, and electrophoresis was performed in a 1.1% agarose gel. Human 28S and 18S rRNAs were used as size markers. The RNA was then transferred to a Zetabind filter and hybridized under high stringent conditions with 32-P-nick translated clone OCI-5. When the RNA was to be isolated from intestines, the tissue was frozen in liquid nitrogen and pulverized before being dissolved in guanidine isothiocyanate.

The Five cDNA Clones Contain a Common 2.2 kb Sequence

DNA was prepared from the 5 selected plaques, and the cloned inserts isolated. All of them had the same size (2.2 kb) suggesting that they contained the same sequence. The 5 inserts were nick translated with 32P and hybridized to a Northern blot containing mRNA (3 μg) extracted from IEC-18, IEC-14, NRK-52E, 15 day old fetal rat intestine, adult rat intestine, and a normal rat fibroblast cell line (Rat-2). The same pattern was obtained with the 5 inserts (a representative blot is shown in FIG. 1) with restriction mapping confirming that the 5 clones contained the same sequence. A single 2.6 kb band was detected in IEC-18 cells but was absent in all the other cell lines. The fetal rat intestine also showed a prominent 2.6 kb band whereas the adult intestine was negative. This last observation indicates that the expression of this 2.6 kb mRNA is developmentally regulated. The insert from one lambda gt10 clone was subsequently cloned into the EcoRI site of plasmid PUC13 and named OCI-5.

Expression Studies of Clone OCI-5 by Northern blot Analysis

Figures 2, 4:
FIG. 2 is a Northern blot analysis of total RNA fractions obtained from rat intestinal cells at different stages of development. The numbers in the left bracket represent days of fetal development, while the numbers in the right bracket represent days after birth. The upper bands represent the expression of the novel intestinal oncofetal gene of the present invention, while the lower and distinct bands represent non-specific hybridization to 18S rRNA.
FIG. 4 is a Northern blot analysis of clone OCI-5 in F9 murine teratocarcinoma cells.

To define the temporal relationship between OCI-5 expression and intestinal development, total RNA (20 μg) was extracted from intestines of embryos and rats of different ages from 15 days of gestation to 24 days postnatal and a Northern blot was performed by hybridization with nick-translated OCI-5. FIG. 2 shows that the expression of clone OCI-5 decreases gradually from day 20 of gestation and finally becomes undetectable after weaning (day 24 post-natal). Numbers in the left bracket represent days of fetal development, while numbers in the right bracket represent days after birth. A tubulin probe was used to confirm that the same amount of RNA was loaded in each lane.

The expression of homologous sequences in other species was investigated. Northern blotting was performed with mRNA extracted from human and murine cells. mRNA (3 μg) from normal human fibroblasts and from cell lines derived from different types of human fibroblasts and from different types of human tumors were probed (FIG. 3) with a) MDA-468, b) SKMG-3, c) HOC-8, d)427-N, e) DLD-1, f) CaCo-2, and g) HT-29. Under high stringency conditions, clone OCI-5 was able to detect 2 bands in CaCo-2, a human colon tumor cell line. The predominant band had the same size as the band detected in rat cells and the less intense band had a size corresponding to 3.0 kb. We could not detect any homologous transcripts in the mRNA of the other cell lines. CaCo-2 cells can acquire enterocytic-like characteristics upon reaching confluency but there was no significant change in the expression of OCI-5 when mRNA was extracted either before or after confluency. The fact that clone OCI-5 detects expression of homologous genes in human and mouse mRNA using high stringency conditions indicates that this gene is highly conserved through evolution. The high level of expression of a homologue of clone OCI-5 in CaCo-2 cells is of considerable interest. This cell line, like HT-29, another human colon tumor cell line, can be induced to differentiate into enterocytic-like cells (Pinto et al. (1982) Biol Cell 44:193-196; Pinto et al. (1983) Biol. Cell 47:323-330. However, CaCo-2 cells, unlike HT29, also express certain antigens that are characteristic of fetal small intestinal cells (Quaroni (1986a) J. Nat. Canc. Inst. 76:571-585). The fact that expression of the clone OCI-5 homologue was observed in CaCo-2 cells, and not in HT-29 cells, indicates that the expression of clone OCI-5 in CaCo-2 is related to the oncofetal characteristics of these cells.

The expression of the murine gene homologous to OCI-5 in F9 teratocarcinoma cells was also investigated. These cells are undifferentiated murine embryonal carcinoma cells which can be induced to differentiate into parietal endoderm or visceral endoderm-like cells. FIG. 4 is a Northern blot analysis where 3 μg of F9 mRNA were hybridized with nick-translated OCI-5 with a) F9 control cells, b) parietal endoderm-like cells, c) visceral endoderm-like cells, and d) IEC-18. The results demonstrate that the undifferentiated F9 cells do not express mRNA homologous to OCI-5 but that a 2.6 kb transcript is detectable after they are induced to differentiate into either parietal or visceral endoderm-like cells. It has been shown previously that the dramatic morphological changes which occur during this differentiation process (Strickland and Mahdavi (1978) supra.) are accompanied by the induction of several proteins involved in the cytoskeletal structure or in cell attachment (Strickland and Mahdavi (1978) supra.; Carlin (1983) J. Biol. Chem. 258:7729-7737.

V-src Infection of IEC-18 Cells

IEC-18 cells were seeded overnight at a density of 100,000 cells per dish in growth medium. The following day different dilutions of SRI, a retrovirus containing the v-src gene which encodes resistance to G-418 were added in the presence of 8 ug of Polybrene per ml of medium. Cells were incubated overnight at 37° C. The following day, the medium was replaced by regular medium. After 48 hrs., 400 mg/ml of G-418 was added. Two weeks later transformed foci were cloned and expanded in the presence of G-418.

Relationship Between Transformation and Expression of Clone OCI-5

The relationship of OCI-5 expression to malignant transformation was investigated by studying different IEC-18 clones induced to become tumorigenic by transfection with the activated human H-ras oncogene (Buick et al. (1987) Exp. Cell Res. 170:300-309). Unlike the parent IEC-18 cells, which are flat and grow with a cobble-stone morphology, the H-ras-transformed cells are spindle-shaped and poorly-adherent. The single stranded DNA from clone OCI-5 was hybridized against mRNA extracted from 3 of these clones, and the 2.6 kb transcript was not identified in any of the transformed clones. (See, FIG. 5A, where lane a) is IEC-18 control and lanes b-d) are three representative transformed clones).

Figures 5A, 5B, 6:
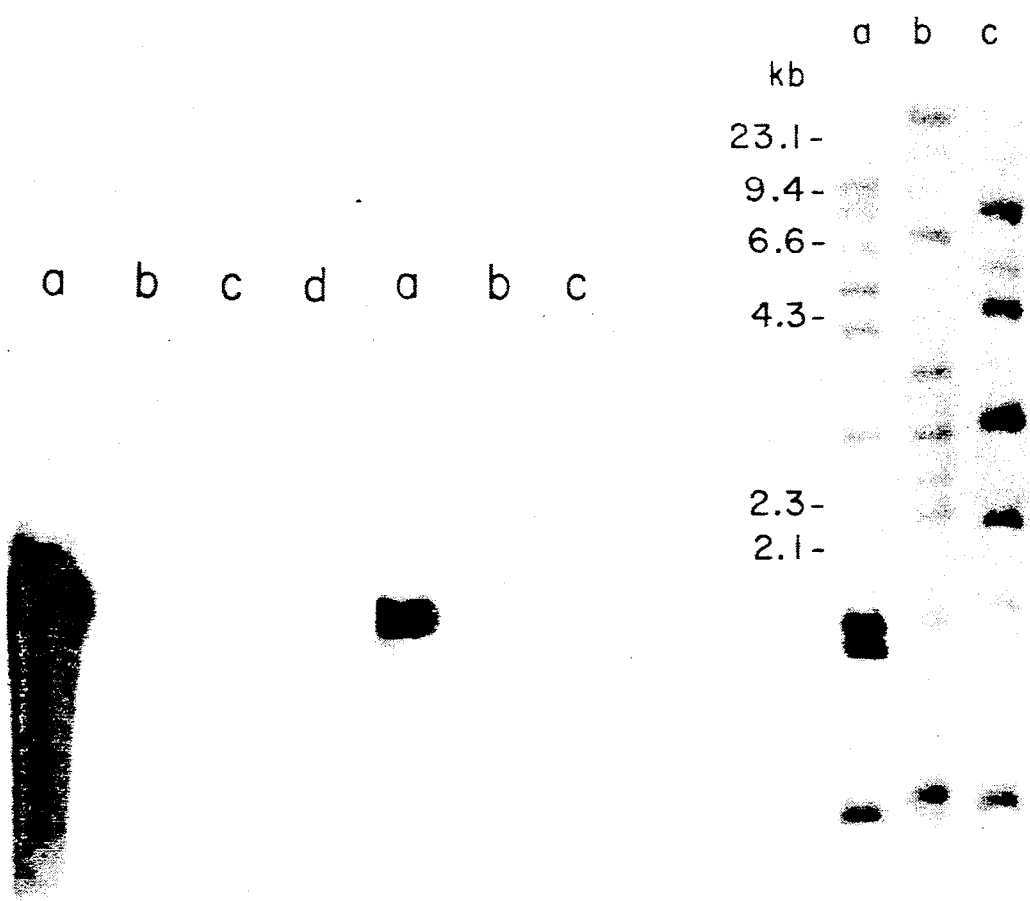
FIG. 6 is a Southern blot analysis of the presence of the novel intestinal oncofetal gene of the present invention in human, mouse, and rat cells, using OCI-5 as a probe.

To investigate whether this dramatic suppression of the expression of clone OCI-5 mRNA was a general event related to transformation, IEC-18 cells were also transformed with a virus containing the V-src gene. V-src transformed clones also displayed a spindle-shaped morphology although the degree of morphological change is less than that seen with H-ras transfected cells. Flat, strongly adherent cells were also seen. mRNA was extracted from two representative V-src infected clones and single stranded DNA from the OCI-5 clone was hybridized to these in a Northern blot analysis. FIG. 5B shows that clone OCI-5 is also down regulated following V-src infection (lane a) is IEC-18 control, and b-c) are two representative transformed clones). These results show that the mRNA coded by clone OCI-5 is down-regulated following transformation with both the src and ras oncogenes, and indicate 1) that expression of this gene in malignant cells is not directly related to viral oncogene expression; and, 2) that expression of the clone OCI-5 gene may be related to cellular morphology which is in turn associated with malignant phenotype.

To determine the expression of the OCI-5 transcript in cell lines and tissues, mRNA was prepared from a rat fibroblast cell line (RAT2); NRK; a scraping of epithelial cells from adult rat intestine (INT); embryonic day 15 rat intestine (EMB); rat intestinal adenocarcinoma cells (RIAC); rat fetal skin (HR), fetal muscle (H9C and A7R), and fetal lung (RFL 6); IEC-18; normal human fibroblasts (427N); human breast cancer cell lines (MDA 468 and MCF7); human glioblastoma bladder urothelium (MGHU); human ovarian carcinoma (OW7); human melanoma (MEWO); human epidermoid carcinoma (A431) and; human colon carcinoma cell lines CaCo-2, HTB-29, and Clone D. OCI-5 was expressed in only IEC-18, RFL-6, EMB, and CaCo-2, as set forth in Table 1.

TABLE 1

Expression of OCI-5 in Cells Tested by Northern Blotting

| Cell Lines | Tissue | Species | Type | Expression |
|---|---|---|---|---|
| RAT2 | | rat | fibroblasts | — |
| NRK | | rat | normal kidney | — |
| FR | | rat | fetal skin | — |
| H9C | | rat | fetal muscle | — |
| A7R | | rat | fetal muscle | — |
| RFL6 | | rat | fetal lung | + |
| IEC-18 | | rat | fetal intestine | + |
| | INT | rat | adult intestine | — |
| | EMB | rat | embryonic intestine | + |
| RIAC | | rat | intestinal adenocarcinoma | — |
| CaCo-2 | | human | colon carcinoma | + |
| HTB 29 | | human | colon carcinoma | — |
| Cline D | | human | colon carcinoma | — |
| H427N | | human | fibroblast | — |
| MDA468 | | human | breast carcinoma | — |
| MCF7 | | human | breast carcinoma | — |
| OW7 | | human | ovarian carcinoma | — |
| SKMG | | human | glioblastoma | — |
| HL60 | | human | promyelocytic leukemia | — |
| MGHu | | human | bladder urothelium | — |
| MEWO | | human | melanoma | — |
| A431 | | human | epidermal carcinoma | — |

Expression of clone OCI-5 in Other Rat Tissues

Expression of the clone OCI-5 was evaluated by Northern blot analysis with mRNA prepared from fetal and adult rat tissues. The results, as shown in Table 2, indicate differential expression of the clone OCI-5 in various tissues during embryonic development. Expression was noted in day 15 fetal lung and liver tissues, with low levels of expression also in muscle and brain tissues on day 15 (Table 2). Low levels of expression could be detected in adult rat lung cells.

TABLE 2

Expression of OCI-5 in Rat Tissues

| Tissue | Development (Days) | Quantity Expressed |
|---|---|---|
| Stomach | d15 | +++ |

TABLE 2-continued

Expression of OCI-5 in Rat Tissues

| Tissue | Development (Days) | Quantity Expressed |
|---|---|---|
| Muscle | adult | ± |
|  | d15 | + |
| Lung | adult | − |
|  | d15 | +++ |
| Liver | adult | + |
|  | d15 | ++ |
| Brain | adult | − |
|  | d15 | + |
| Kidney | adult | ± |
| Colon | adult | + |
|  | adult | − |

Expression of OCI-5 in Intestinal Cell Lines

Although the OCI-5 transcript is abundant in IEC-18 cells, this is not a general feature of all of the IEC cell lines. The expression of the clone OCI-5 was investigated with Northern blotting in rat IEC 6, 14, 17, 18, 19, and 20 intestinal cell lines. Expression was observed in cell lines IEC-17-20 (Table 3), and a wide range of expression was observed in different IEC cell lines. It is possible that this expression is related to differences in the differentiation state or the cellular origin of these different cell lines. Two human colon carcinoma cell lines expressed OCI-5 (CaCo-2 and T-84).

TABLE 3

Expression of OCI-5 in Rat Intestinal Cell Lines (IEC) and Human Colonic Cancer Cell Lines

| Cell Line | Derived From: | Expression |
|---|---|---|
| IEC-6 | suck.rat-sm.int. | − |
| IEC-14 | suck.rat-sm.int. | − |
| IEC-17 | suck.rat-duodenum | ++ |
| IEC-18 | suck.rat-ileal | +++ |
| IEC-19 | fetal-d.14 | + |
| IEC-20 | fetal-d.14 | + |
| CaCo-2 | colon carcinoma | +++ |
| T84 | colon carcinoma | ++ |
| SW948 | colon carcinoma | − |
| HTB-29 | colon carcinoma | − |
| OLD-1 | colon carcinoma | − |

DNA isolation and Blotting

Genomic DNA was isolated by SDS-proteinase K lysis, organic extraction, and NaCl-ethanol precipitation. DNA was digested with HindIII, electrophoresed in 0.8% agarose gel, and transferred to a Zetabind membrane. Clone OCI-5 was 32P-nick translated and hybridization was performed at 42° C. in 5X SSC, 1X Denhardts solution, 100 µg/ml of denatured salmon sperm DNA, 0.1% SDS, 20 mM sodium phosphate and 30% formamide.

Human and Murine Genomic Organization of Clone OCI-5 by Southern blot Analysis Northern blotting of RNA from CaCo-2 human tumor cells and F9 murine teratocarcinoma cells (above) suggests the presence of human and murine homologues of the OCI-5 gene. This was investigated further by Southern blotting of DNA from rat, mouse and human cells. Under conditions of moderate stringency, OCN-5 (10 µg) is able to detect 10 bands in rat DNA (lane c), 11 bands in human DNA (lane b), and 7 bands in mouse DNA (lane a) after restriction with HindIII (FIG. 6). Southern blot analysis detects DNA fragments which add up to a total of 70 kb of human DNA, 40 kb of rat DNA, or 36 kb of mouse DNA.

These results suggest the presence of a widely conserved genomic family related to OCI-5, in a manner similar to that seen with the cytokeratin gene family.

DNA Sequencing

EcoRI, PstI, HindIII and SstI fragments of clone OCI-5 were purified from an agarose gel and cloned into bacteriophage M13 mp18 vector (Messing and Vieira (1982) Gene 19:269-276). Single stranded DNA templates were prepared as described previously (Sanger et al. (1980) J. Mol. Biol. 143:161-178) and sequenced by the dideoxynucleotide chain termination method (Sanger et al. (1977) PNAS USA 74:5463-5467). The sequence analysis was completed by the use of 7 specific oligonucleotide primers as indicated by asterisks in FIG. 7.

DNA Sequence of Clone OCI-5

Figure 7:
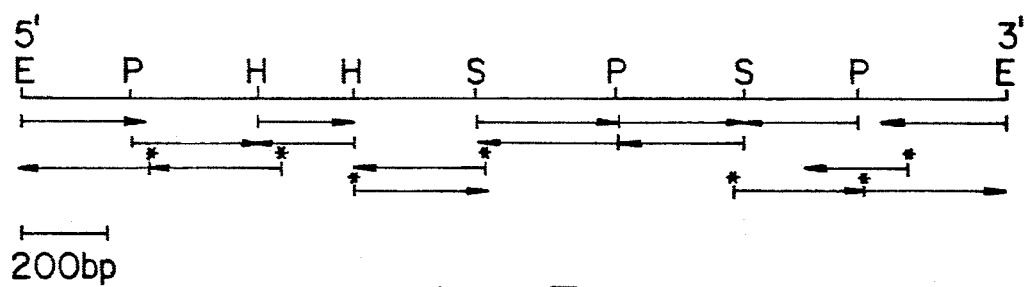
FIG. 7 is a partial restriction map of OCI-5 which illustrates the oligonucleotide primers used in sequence analysis of OCI-5.

Both strands of clone OCI-5 were sequenced. FIG. 7 shows a partial restriction map of clone OCI-5 and the sequencing strategy employed for both strands. One strand showed an open reading frame of 1,856 bases with the first methionine 69 bases after the last in-frame stop codon. FIG. 8 shows the sequence of that strand and its translation product starting from the first methionine codon. The translation product will consist of 597 amino acids (69,337 daltons in molecular weight). Since the nucleotide sequence surrounding the first ATG diverges significantly from the consensus sequence for eukaryotic initiation sites (Kozak (1984) Nucleic Acids Res 12:857-872) the estimated length is tentative.

Since the transcript detected by clone OCI-5 is approximately 300 bp longer than the insert itself, it is evident that non-translated sequences are missing from OCI-5. The additional sequences probably extend to the 5' end of the insert, since there is a polyadenylation site and a short poly(A) tail at the 3' end. The predicted protein sequence included 3 potential glycosylation sites but a candidate transmembrane domain (at least 20 consecutive hydrophobic residues) was not found. The amino acid hydropathicity plot shows two mildly hydrophobic regions, one near the putative amino terminus and the other near the carboxyl terminus (data not shown). A computer search of the National Biological Research Foundation protein sequence database (release 15.0, December, 1987) detected no strong homology with any of the 7,000 published amino acid sequences.

Although the foregoing invention has been described in some detail by way of illustration and example for purposes of clarity of understanding, it will be obvious that certain changes and modifications may be practiced within the scope of the appended claims.

What is claimed is:

1. An isolated DNA or RNA molecule having a nucleotide sequence encoding intestinal oncofetal gene and identical to that set forth in FIG. 8.

2. An isolated DNA or RNA molecule having a length in the range of 15 to 5,000 nucleotides and capable of hybridizing under high stringency to the intestinal oncofetal gene having the DNA sequence set forth in FIG. 8.

3. An isolated DNA or RNA molecule having a length in the range of 15 to 5,000 nucleotides and capable of hybridizing under high stringency to the intestinal oncofetal gene having the DNA sequence set forth in FIG. 8 and possessing a detectable label selected from the group consisting of $^3H$, $^{125}I$, $^{35}S$, $^{14}C$ and $^{32}P$.

4. A cDNA clone designated OCI-5 and having A.T.C.C. accession no. 40481.

* * * * *